(12) United States Patent
Kotsugai et al.

(10) Patent No.: US 11,199,528 B2
(45) Date of Patent: Dec. 14, 2021

(54) SENSOR BUILT-IN FILTER STRUCTURE AND WAFER ACCOMMODATION CONTAINER

(71) Applicant: TDK CORPORATION, Tokyo (JP)

(72) Inventors: Tatsuhiro Kotsugai, Tokyo (JP); Toshihiko Miyajima, Tokyo (JP); Takeshi Kagaya, Tokyo (JP)

(73) Assignee: TDK CORPORATION, Tokyo (JP)

( * ) Notice: Subject to any disclaimer, the term of this patent is extended or adjusted under 35 U.S.C. 154(b) by 165 days.

(21) Appl. No.: 16/524,251

(22) Filed: Jul. 29, 2019

(65) Prior Publication Data

US 2020/0033308 A1     Jan. 30, 2020

(30) Foreign Application Priority Data

Jul. 30, 2018  (JP) .............................. JP2018-142848

(51) Int. Cl.
| | |
|---|---|
| *G01N 33/00* | (2006.01) |
| *H01L 21/673* | (2006.01) |
| *G01N 1/40* | (2006.01) |
| *G01N 7/10* | (2006.01) |

(52) U.S. Cl.
CPC ......... *G01N 33/0011* (2013.01); *G01N 1/405* (2013.01); *G01N 7/10* (2013.01); *G01N 33/0029* (2013.01); *G01N 33/0047* (2013.01); *H01L 21/67389* (2013.01); *G01N 2001/4016* (2013.01)

(58) Field of Classification Search
CPC ...... G01N 7/10; G01N 33/0011; G01N 1/405; G01N 33/0047; G01N 2001/4016
USPC ....................................................... 73/31.07
See application file for complete search history.

(56) References Cited

U.S. PATENT DOCUMENTS

| | | | | | |
|---|---|---|---|---|---|
| 4,924,890 A | * | 5/1990 | Giles | ................. | H01L 21/67028 134/61 |
| 5,252,133 A | * | 10/1993 | Miyazaki | .............. | C23C 16/455 118/725 |
| 5,255,783 A | * | 10/1993 | Goodman | ......... | H01L 21/67393 206/711 |
| 5,277,579 A | * | 1/1994 | Takanabe | .............. | C30B 35/005 432/5 |
| 5,320,218 A | * | 6/1994 | Yamashita | ........ | H01L 21/67393 206/213.1 |
| 5,351,415 A | * | 10/1994 | Brooks | ................ | F26B 21/003 141/85 |
| 5,373,806 A | * | 12/1994 | Logar | ..................... | C30B 25/10 117/106 |
| 5,433,574 A | * | 7/1995 | Kawano | .................... | B01L 1/04 414/217 |

(Continued)

FOREIGN PATENT DOCUMENTS

| | | | | | |
|---|---|---|---|---|---|
| JP | 2002122382 | * | 4/2002 | ............ | B01D 53/26 |
| JP | 2003-347397 A | | 12/2003 | | |

(Continued)

*Primary Examiner* — Clayton E. LaBalle
*Assistant Examiner* — Kevin C Butler
(74) *Attorney, Agent, or Firm* — Oliff PLC (57) ABSTRACT

Provided is sensor built-in filter structure arranged in a wafer accommodation container, comprising: a first filter; a second filter arranged closer to a wafer accommodation chamber of the wafer accommodation container than to the first filter; and a gas detection sensor arranged between the first filter and the second filter to detect a state of a gas.

15 Claims, 7 Drawing Sheets

(56) References Cited

U.S. PATENT DOCUMENTS

| | | | | |
|---|---|---|---|---|
| 5,482,161 A * | 1/1996 | Williams | H01L 21/67369 | 206/711 |
| 5,536,320 A * | 7/1996 | Ushikawa | C23C 16/4401 | 118/719 |
| 5,879,458 A * | 3/1999 | Roberson, Jr. | H01L 21/67775 | 118/715 |
| 5,988,233 A * | 11/1999 | Fosnight | H01L 21/67393 | 141/63 |
| 6,053,688 A * | 4/2000 | Cheng | H01L 21/67772 | 118/719 |
| 6,135,168 A * | 10/2000 | Yang | H01L 21/67373 | 141/91 |
| 6,364,922 B1 * | 4/2002 | Tanaka | H01L 21/67393 | 206/710 |
| 6,393,334 B1 * | 5/2002 | Lewis | H01L 21/67379 | 700/117 |
| 6,588,123 B2 * | 7/2003 | Chen | H01L 21/67017 | 34/389 |
| 6,899,145 B2 * | 5/2005 | Aggarwal | H01L 21/67393 | 141/11 |
| RE39,241 E * | 8/2006 | Fosnight | B01D 46/008 | 141/98 |
| 8,522,836 B2 * | 9/2013 | Okabe | H01L 21/67393 | 141/286 |
| 8,783,463 B2 * | 7/2014 | Watson | H01L 21/67393 | 206/710 |
| 8,870,512 B2 * | 10/2014 | Rice | H01L 21/67386 | 414/217 |
| 9,054,144 B2 | 6/2015 | Burns | H01L 21/67393 | |
| 9,105,673 B2 | 8/2015 | Babbs | H01L 21/67213 | |
| 9,257,320 B2 * | 2/2016 | Fosnight | H01L 21/67389 | |
| 9,403,196 B2 * | 8/2016 | Rioufrays | H01L 21/67389 | |
| 9,704,727 B2 | 7/2017 | Segawa | H01L 21/67772 | |
| 9,779,972 B2 | 10/2017 | Favre | H01L 21/67253 | |
| 9,837,293 B2 * | 12/2017 | Lai | H01L 21/67389 | |
| 9,895,723 B2 * | 2/2018 | Iwamoto | H01L 21/67775 | |
| 9,929,033 B2 | 3/2018 | Emoto | H01L 21/67389 | |
| 9,997,388 B2 | 6/2018 | Smith | B65D 85/38 | |
| 10,014,200 B2 | 7/2018 | Murata | H01L 21/67389 | |
| 10,395,948 B2 * | 8/2019 | Oh | H01L 21/02 | |
| 10,553,468 B2 * | 2/2020 | Itakura | H01L 21/67389 | |
| 10,646,947 B2 * | 5/2020 | Ennsbrunner | B23K 9/32 | |
| 10,777,437 B2 | 9/2020 | Fukasawa | H01L 21/67017 | |
| 10,790,177 B2 | 9/2020 | Lin | H01L 21/67253 | |
| 10,818,529 B2 * | 10/2020 | Murata | H01L 21/67389 | |
| 10,847,395 B2 | 11/2020 | Woo | H01L 21/67393 | |
| 10,903,103 B2 | 1/2021 | Kuan | H01L 21/67772 | |
| 10,923,373 B2 * | 2/2021 | Ogawa | H01L 21/673 | |
| 2002/0028399 A1 * | 3/2002 | Nakasuji | H01J 37/266 | 430/30 |
| 2004/0168742 A1 * | 9/2004 | Kim | H01L 21/67017 | 141/98 |
| 2005/0160705 A1 * | 7/2005 | Bernard | H01L 21/67155 | 55/385.1 |
| 2007/0023322 A1 * | 2/2007 | Hyun | H01L 21/67772 | 206/711 |
| 2007/0144118 A1 * | 6/2007 | Alvarez, Jr. | H01L 21/67017 | 55/385.1 |
| 2009/0064760 A1 * | 3/2009 | Moriya | H01L 21/67253 | 73/28.04 |
| 2009/0142166 A1 * | 6/2009 | Miyajima | H01L 21/67772 | 414/217.1 |
| 2010/0059408 A1 * | 3/2010 | Igarashi | H01L 21/67772 | 206/710 |
| 2010/0117377 A1 * | 5/2010 | Okabe | E05B 17/0029 | 292/159 |
| 2010/0133270 A1 * | 6/2010 | Okabe | H01L 21/67772 | 220/212 |
| 2010/0280653 A1 * | 11/2010 | Aburatani | H01L 21/67265 | 700/228 |
| 2014/0325772 A1 * | 11/2014 | Jhon | H01L 21/67028 | 15/97.1 |
| 2015/0101482 A1 * | 4/2015 | Chou | B01D 46/442 | 95/12 |
| 2015/0107770 A1 * | 4/2015 | Choi | H01L 21/67028 | 156/345.29 |
| 2015/0170939 A1 * | 6/2015 | Rebstock | B08B 9/0321 | 137/15.04 |
| 2015/0206780 A1 * | 7/2015 | Choi | H01L 21/67017 | 206/710 |
| 2015/0276572 A1 * | 10/2015 | Thovex | H01L 21/67389 | 73/37 |
| 2015/0301007 A1 * | 10/2015 | Thovex | H01L 21/673 | 73/23.2 |
| 2015/0364346 A1 * | 12/2015 | Woo | H01L 21/67781 | 15/405 |
| 2016/0284580 A1 * | 9/2016 | Woo | H01L 21/67393 | |
| 2017/0011942 A1 * | 1/2017 | Woo | H01L 21/67724 | |
| 2017/0069516 A1 * | 3/2017 | Chen | B05B 9/01 | |
| 2017/0178942 A1 * | 6/2017 | Sakata | H01L 21/68707 | |
| 2018/0148834 A1 * | 5/2018 | Kamimura | H01L 21/67313 | |
| 2018/0233392 A1 * | 8/2018 | Abe | H01L 21/67389 | |
| 2019/0035660 A1 * | 1/2019 | Lin | H01L 21/67769 | |
| 2019/0393056 A1 * | 12/2019 | Hirochi | H01L 21/67769 | |
| 2020/0033308 A1 * | 1/2020 | Kotsugai | H01L 21/67253 | |
| 2020/0101624 A1 * | 4/2020 | Sakata | H01L 21/67766 | |
| 2020/0105560 A1 * | 4/2020 | Chen | B05B 15/52 | |
| 2020/0161146 A1 * | 5/2020 | Goldberg | H01L 21/68764 | |
| 2020/0201363 A1 * | 6/2020 | Hruzek | F16K 27/003 | |
| 2020/0219744 A1 * | 7/2020 | Kim | H01L 21/67775 | |
| 2020/0234988 A1 * | 7/2020 | Lin | H01L 21/67775 | |

FOREIGN PATENT DOCUMENTS

| | | | | |
|---|---|---|---|---|
| JP | 2003347397 | * | 12/2003 | B08B 5/00 |
| WO | WO-9928952 A2 | * | 6/1999 | H01L 21/67265 |

* cited by examiner

SENSOR BUILT-IN FILTER STRUCTURE AND WAFER ACCOMMODATION CONTAINER

BACKGROUND OF THE INVENTION

1. Field of the Invention

The present invention relates to a sensor built-in filter structure arranged in a flow path for introducing a cleaning gas into a wafer accommodation chamber or discharging a gas from the wafer accommodation chamber in a wafer accommodation container and a wafer accommodation container having the sensor built-in filter structure.

2. Description of the Related Art

For example, in a semiconductor manufacturing process, a wafer accommodation container called a SMIF or a FOUP is used to transport a wafer between processing apparatuses and store the wafer.

Herein, in order to protect a wafer surface from oxidation and contamination, it is preferable that the environment in the wafer accommodation container in which the wafer is accommodated is maintained in an inactive state and a degree of cleanliness higher than a predetermined state. As a method for improving the inactive state of the gas and the degree of cleanliness in the container, techniques such as gas purge of introducing a cleaning gas into the interior of the container or a space communicating with the container have been proposed. Meanwhile, as a technique of maintaining the degree of the cleanliness in the container to a predetermined state, techniques of controlling water concentration and oxygen concentration in the wafer accommodation container by connecting pipes to the container and circulating the gas between the interior of the container and an external environment control unit have been proposed (refer to JP 2003-347397 A).

However, in the method of controlling by extracting the gas in the accommodation container to the outside in the related art, there are problems in that the degree of cleanliness in the accommodation container cannot be detected unless the gas in the accommodation container is once extracted to the outside, and it is difficult to shorten the detection time. On the other hand, in the method of providing a detection mechanism such as a sensor inside the wafer accommodation chamber accommodating a wafer, there is a problem in that the detection mechanism is flooded at the time of rinsing the wafer accommodation chamber, and thus, the rinsing needs to be performed after the removal of the detection mechanism, so that there is a problem in terms of maintenance performance.

SUMMARY OF THE INVENTION

The invention has been considered in the above situation, and an object is to provide a sensor built-in filter structure capable of detecting a degree of cleanliness of a wafer accommodation chamber and maintaining good maintenance performance of the wafer accommodation container and a wafer accommodation container having the sensor built-in filter structure.

According to an aspect of the invention, there is provided a sensor built-in filter structure arranged in a flow path communicating with a wafer accommodation chamber in a wafer accommodation container, the sensor built-in filter structure including: a first filter removing dust contained in a gas; a second filter arranged closer to the wafer accommodation chamber than to the first filter to block passage of water as a liquid and to allow the gas to pass; and a gas detection sensor arranged between the first filter and the second filter to detect at least one of temperature, humidity, pressure, and components of the contacted gas or dust in the gas.

Since the sensor built-in filter structure according to the invention is provided in the flow path connected to the wafer accommodation chamber, and the second filter on the side closer to the wafer accommodation chamber allows the gas to pass, the built-in gas detection sensor can easily detect the gas in the wafer accommodation chamber. In addition, since the second filter arranged on the wafer accommodation chamber side blocks passage of water as a liquid, it is possible to prevent the gas detection sensor from being flooded, for example, even at the time of rinsing the wafer accommodation chamber with water. Therefore, such a sensor built-in filter structure has little adverse effect on the maintenance performance of the wafer accommodation container, and the wafer accommodation chamber can be rinsed even in a state where the sensor is attached. In addition, since the first filter of the external side removes dust contained in the gas, external dust can be prevented from flowing into the wafer accommodation chamber, and thus, it is possible to prevent the problem of dust in the wafer accommodation chamber from flowing out.

In addition, it is preferable that the first filter has a particle collection rate higher than that of the second filter, and it is preferable that the second filter has a water resistance higher than that of the first filter.

In addition, for example, the first filter and the second filter may be arranged with a predetermined interval, and the gas detection sensor may be provided on a surface of the first filter on a side closer to the wafer accommodation chamber.

Such a sensor built-in filter structure can more preferably prevent the gas detection sensor or the first filter from being in contact with water.

In addition, for example, the first filter and the second filter may be arranged with a predetermined interval, and the gas detection sensor may be provided on a surface of the second filter on a side opposite to the wafer accommodation chamber.

Such a sensor built-in filter structure can suitably prevent the first filter from being in contact with water, and the gas detection sensor can be arranged closer to the wafer accommodation chamber.

In addition, for example, the first filter and the second filter may be overlapped with the gas detection sensor interposed between the first filter and the second filter.

With such a structure, the sensor built-in filter structure can be thinned.

In addition, for example, the second filter may have a smaller area than the first filter and may be provided on a surface of the gas detection sensor on a side closer to the wafer accommodation chamber.

In the sensor built-in filter structure having such a structure, since the second filter has a small area, it is possible to reduce pressure loss of the flow path in which the sensor built-in filter structure is arranged.

In addition, for example, according to an aspect of the invention, there is provided a wafer accommodation container including: the sensor built-in filter structure according to any one of the above sensor built-in filter structures; the wafer accommodation chamber; and a purge port having a flow path for introducing a cleaning gas into the wafer accommodation chamber or for discharging a gas from the wafer accommodation chamber.

In such a wafer accommodation container, since the sensor built-in filter structure is arranged in the flow path of the purge port, it is possible to easily detect the gas in the wafer accommodation chamber, and the space for arranging the gas detection sensor is also used as the flow path of the purge port, which is advantageous from the viewpoint of miniaturization.

In addition, for example, the flow path in which the sensor built-in filter structure is provided may be a portion of the purge port for discharging a gas from the wafer accommodation chamber.

Since the sensor built-in filter structure is arranged in the flow path of the purge port for discharging the gas from the wafer accommodation chamber, such a wafer accommodation container can suitably detect a degree of cleanliness of the wafer accommodation chamber even during purge.

DETAILED DESCRIPTION OF THE PREFERRED EMBODIMENTS

Hereinafter, the invention will be described on the basis of embodiments illustrated in the drawings.

Figure 1:
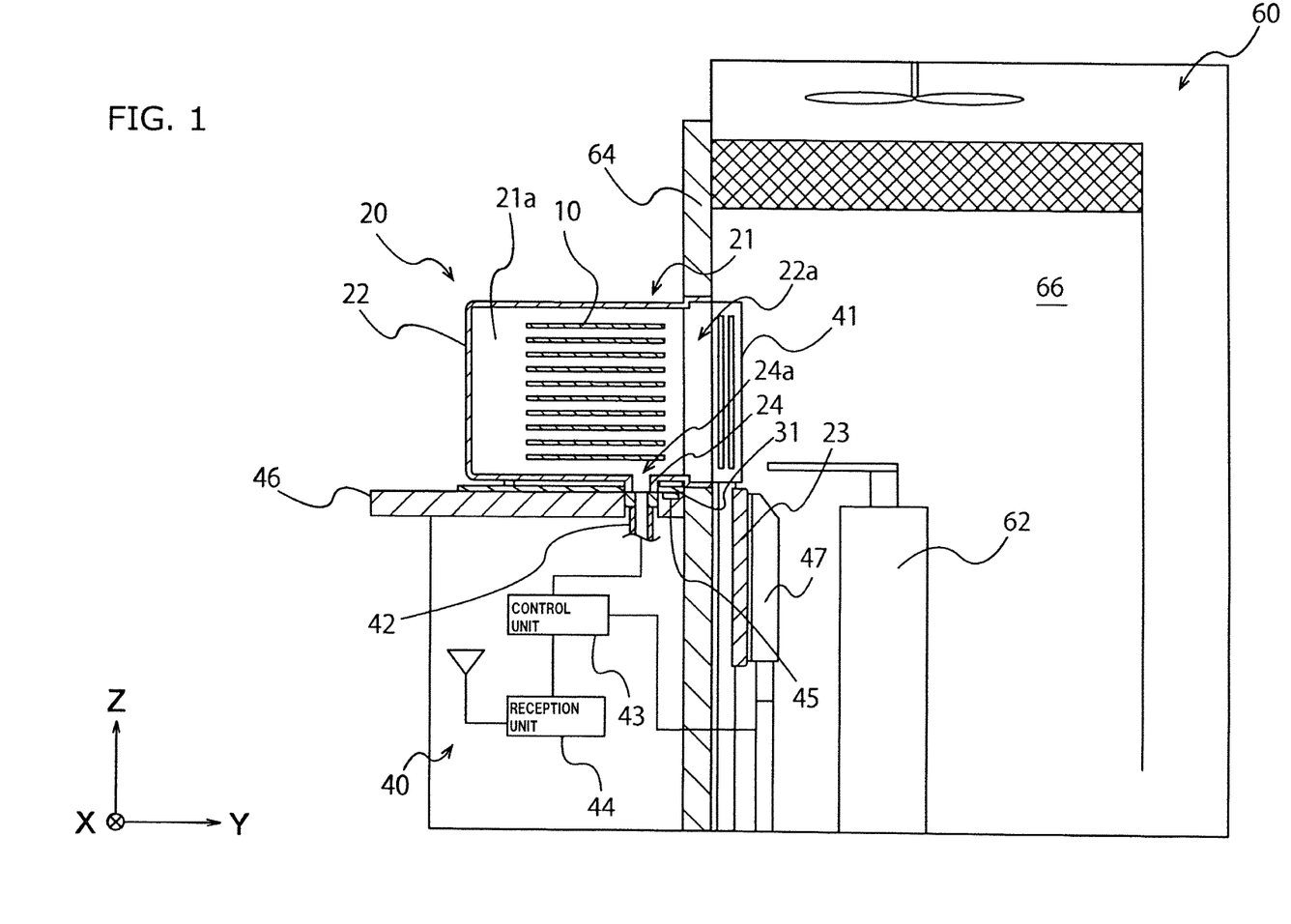
FIG. 1 is a schematic view illustrating a state where a wafer accommodation container including a sensor built-in filter structure according to an embodiment of the invention is mounted on a load port device.

FIG. 1 is a schematic view illustrating a state where a FOUP 20 as a wafer accommodation container including a sensor built-in filter structure 50 (hereinafter also referred to as a "filter structure 50") according to an embodiment of the invention is mounted on a load port device 40. As described later, the filter structure 50 is arranged in a flow path 24a connected from the external load port device 40 to a wafer accommodation chamber 21a in the FOUP 20. In addition, the detailed structure of the filter structure 50 will be described later with reference to FIG. 5 and the like, and thus, the structure of the filter structure 50 is not illustrated in FIG. 1.

The load port device 40 constitutes a portion of an EFEM 60 for taking out a wafer 10 from the inside of the FOUP 20 and transporting the wafer 10 to a semiconductor processing apparatus (not illustrated). The load port device 40 is provided to a wall portion 64 of a wafer transfer chamber 66 formed in the EFEM 60 to function as a portion of an interface for moving the wafer 10 to a semiconductor processing chamber. The inside of the wafer transfer chamber 66 of the EFEM 60 is maintained in a constant clean environment by using a fan filter unit and the like. In addition, a transfer robot 62 and the like having a robot arm for taking out the wafer 10 from the FOUP 20 is provided in the wafer transfer chamber 66.

The load port device 40 includes a mounting table 46 on which the FOUP 20 is installed. The FOUP 20 that seals, accommodates, and transfers the wafer 10 can be detachably mounted on the top of the mounting table 46 in the Z-axis direction. In addition, the mounting table 46 is moved in a state where the FOUP 20 is mounted, so that the FOUP 20 can be connected to the wafer transfer chamber 66. In addition, in the drawings, the Y axis indicates the moving direction of the mounting table 46, the Z axis indicates the up/down direction as the vertical direction, and the X axis indicates a direction perpendicular to the Y axis and the Z axis.

The load port device 40 illustrated in FIG. 1 has a door 47 for opening a lid 23 of the FOUP 20. When the FOUP 20 is mounted on the mounting table 46, first, the load port device 40 moves the FOUP 20 to a position where a portion of the FOUP 20 is engaged with an opening of the wall portion 64, by moving the mounting table 46. After that, the load port device 40 opens the lid 23 of the FOUP 20 by using the door 47. Accordingly, the load port device 40 can connect the wafer accommodation chamber 21a accommodating the wafer 10 in the FOUP 20 and the wafer transfer chamber 66 in a sealed manner through a main opening 22a of a housing unit 22.

In addition, the load port device 40 illustrated in FIG. 1 also functions as a cleaning device inside the wafer accommodation container, which cleans the interior of the FOUP 20 which is the wafer accommodation container. The load port device 40 includes a front purge nozzle 41 that performs cleaning from the main opening 22a of the FOUP 20 and a bottom purge nozzle 42 that performs cleaning from a bottom extraction port 24 and a bottom introduction port 25 that are purge ports of the FOUP 20. The front purge nozzle 41 is arranged in the vicinity of the main opening 22a connected to the wafer transfer chamber 66. The front purge nozzle 41 releases the cleaning gas toward the main opening 22a of the FOUP 20 and introduces the cleaning gas into the FOUP 20. In addition, the cleaning gas for cleaning the interior of the FOUP 20 is not particularly limited. However, an inert gas such as a nitrogen gas, or dry air may be exemplified, and the nitrogen gas is preferable.

The bottom purge nozzle 42 protrudes from the mounting table 46 and is connected to the bottom extraction port 24 or the bottom introduction port 25 provided at the bottom of the FOUP 20. Although illustration is simplified in FIG. 1, the bottom purge nozzle 42 includes an introduction nozzle connected to the bottom introduction port 25 (refer to FIG. 2) of the FOUP 20 and a discharge nozzle connected to the bottom extraction port 24 (refer to FIG. 2) of the FOUP 20. The introduction nozzle of the bottom purge nozzle 42 releases the cleaning gas and introduces the cleaning gas into the wafer accommodation chamber 21a through the bottom introduction port 25 of the FOUP 20. In addition, at the same time as the introduction nozzle releases the cleaning gas, the discharge nozzle of the bottom purge nozzle 42 can discharge the gas in the wafer accommodation chamber 21a through the bottom extraction port 24 of the FOUP 20. Accordingly, the load port device 40 having the bottom purge nozzle 42 can efficiently clean the atmosphere of the wafer accommodation chamber 21a.

The introduction of the cleaning gas by the front purge nozzle 41 and the bottom purge nozzle 42 is controlled by a control unit 43 of the load port device 40. For example, the control unit 43 controls the introduction of the cleaning gas into the FOUP 20 by opening and closing a solenoid valve provided in a piping portion that supplies the cleaning gas to the front purge nozzle 41 and the bottom purge nozzle 42. In addition, the control unit 43 may control the introduction of the cleaning gas into the FOUP 20 by adjusting the flow rate of the gas discharged from the FOUP 20 by using the discharge nozzle of the bottom purge nozzle 42. In addition, the exhaust of the gas in the FOUP 20 by the bottom purge nozzle 42 may be forced exhaust or natural exhaust.

As described later, the FOUP 20 is provided with a detection mechanism 30, and the load port device 40 includes a reception unit 44 in communication with the detection mechanism 30 of the FOUP 20. The reception unit 44 receives information such as the detection result of the atmosphere in the FOUP 20. The reception unit 44 includes a modem or the like to be capable of communicating with at least a transmission unit 32 (refer to FIG. 6) of the detection mechanism 30 provided to the FOUP 20 mounted on the mounting table 46. In addition, the reception unit 44 can transmit various signals including a control signal to the transmission unit 32 of the detection mechanism 30.

In FIG. 1, the FOUP 20 mounted on the mounting table 46 of the load port device 40 is a container for accommodating and storing the wafer 10 in the semiconductor factory and the like or transporting the wafer 10 between the devices in the semiconductor factory. The FOUP 20 includes a wafer accommodation unit 21 having an outer shape of a box (substantially rectangular parallelepiped), and the wafer accommodation chamber 21a for accommodating the wafer 10 is formed inside the wafer accommodation unit 21.

Figure 2:
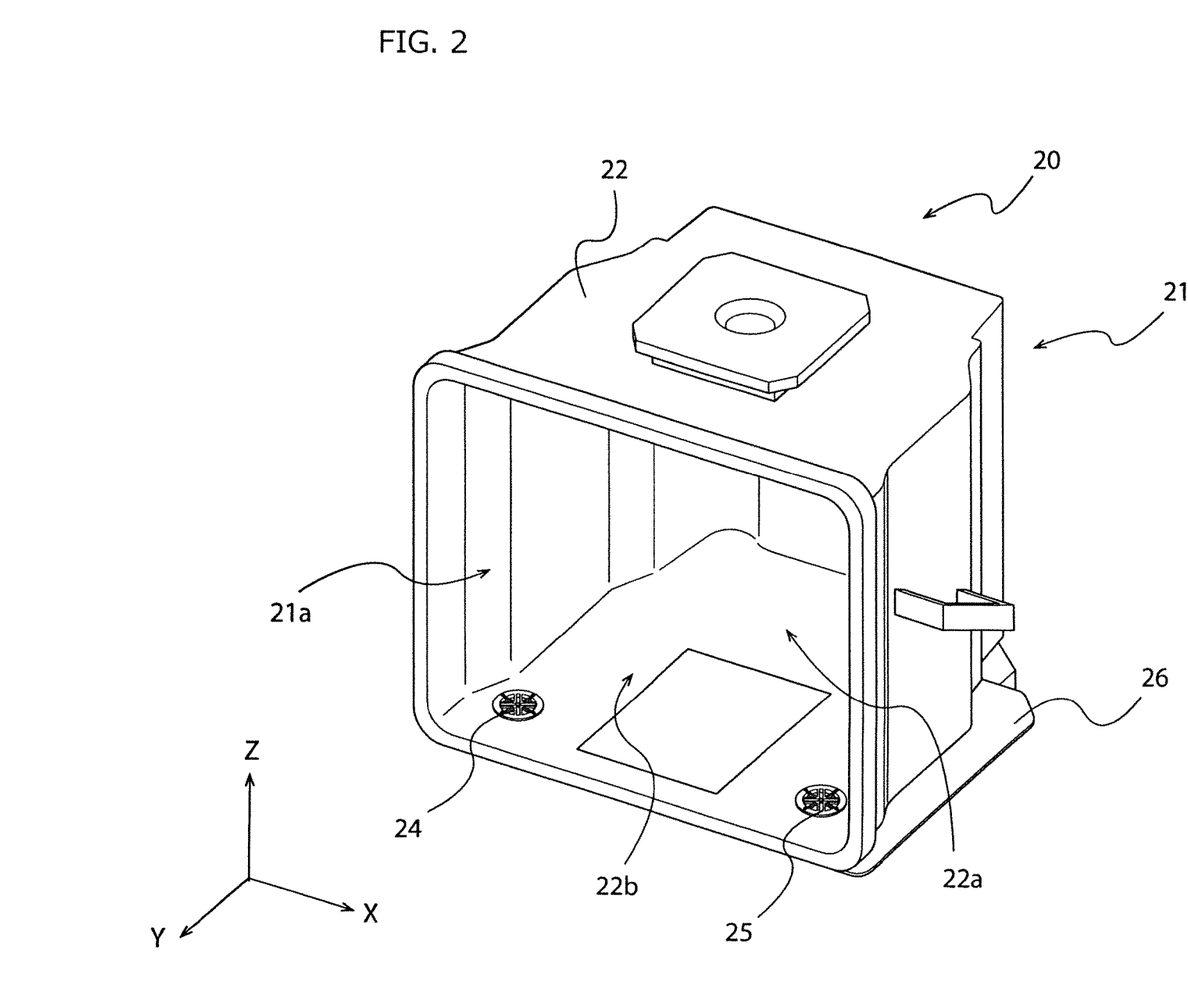
FIG. 2 is an external view illustrating a wafer accommodation chamber of the wafer accommodation container illustrated in FIG. 1.

As illustrated in FIG. 1, the wafer accommodation unit 21 includes a housing unit 22 and a lid 23 that is detachable from the housing unit 22. As illustrated in FIG. 2 which is a perspective view of the FOUP 20 in a state where the lid 23 is removed, the main opening 22a for unloading the wafer 10 from the wafer accommodation chamber 21a and loading the wafer 10 into the wafer accommodation chamber 21a is formed on the side surface of the housing unit 22. A rack (not illustrated) for vertically stacking a plurality of horizontally retained wafers 10 is arranged inside the housing unit 22. The wafers 10 mounted on the rack are accommodated inside the FOUP 20 with a constant interval.

As illustrated in FIG. 1, the lid 23 is detachably provided to the main opening 22a of the housing unit 22. The load port device 40 can open the main opening 22a of the housing unit 22 by engaging the door 47 with the lid 23 and moving the door 47 engaged with the lid 23 into the wafer transfer chamber 66.

As illustrated in FIG. 2, the housing unit 22 has an accommodation-unit bottom wall 22b which is a bottom wall of the wafer accommodation unit 21. The accommodation-unit bottom wall 22b is integrally formed with the side wall and the top wall of the wafer accommodation unit 21. When the main opening 22a of the housing unit 22 is closed by the lid 23, the wafer accommodation chamber 21a accommodating the wafer 10 is surrounded by the accommodation-unit bottom wall 22b, the side wall, and the top wall of wafer accommodation unit 21 and the lid 23 to become a sealed space.

As illustrated in FIG. 2, the accommodation-unit bottom wall 22b is provided with two purge ports of a bottom extraction port 24 and a bottom introduction port 25. The flow path 24a connected from the outside to the wafer accommodation chamber 21a is formed Inside the bottom extraction port 24 and the bottom introduction port 25. That is, the introduction nozzle of the bottom purge nozzle 42 illustrated in FIG. 1 is connected to the bottom introduction port 25 from the below, and the cleaning gas is introduced into the wafer accommodation chamber 21a through the flow path formed inside the bottom introduction port 25.

In addition, the discharge nozzle of the bottom purge nozzle 42 is connected to the bottom extraction port 24 from the below, and the gas of the wafer accommodation chamber 21a is discharged to the outside of the FOUP 20 through the flow path 24a formed inside the bottom extraction port 24.

As illustrated in FIG. 2, the FOUP 20 has a bottom plate 26 provided below the accommodation-unit bottom wall 22b. A plurality of through holes are formed in the bottom plate 26 so that the bottom purge nozzle 42 of the load port device 40 can be connected to the bottom extraction port 24 and the bottom introduction port 25 of the FOUP 20. In addition, an engaging portion or the like that is engaged with a positioning pin 48 that positions the FOUP 20 with respect to the mounting table 46 is formed in the bottom plate 26.

Figure 3:
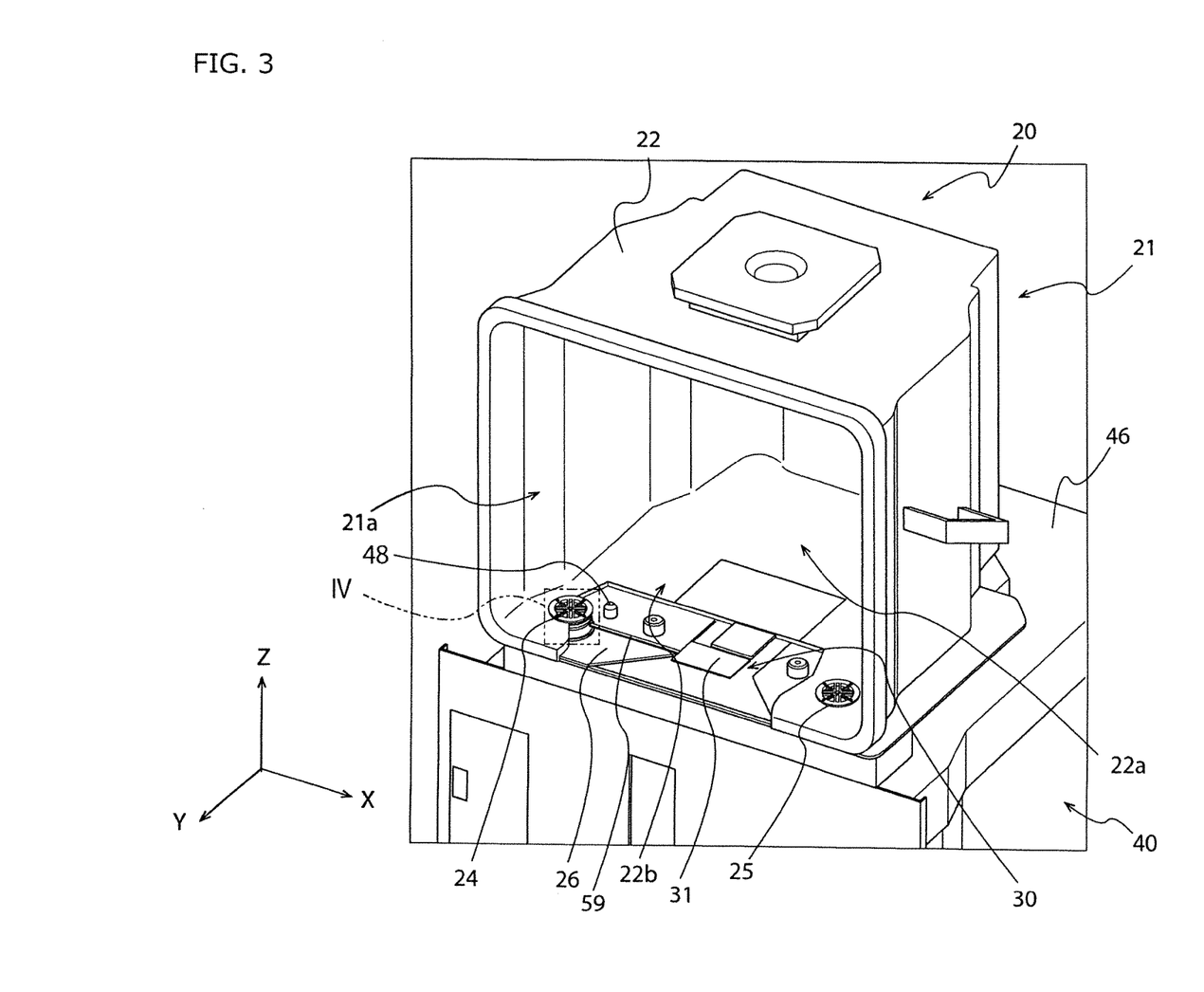
FIG. 3 is a partial cross-sectional view illustrating a detection mechanism included in the wafer accommodation container illustrated in FIG. 1.

FIG. 3 is a partial cross-sectional view illustrating a portion of the accommodation-unit bottom wall 22b of the FOUP 20 mounted on the mounting table 46. As illustrated in FIG. 3, the FOUP 20 includes a detection mechanism 30 which detects the state and the like of the gas in the wafer accommodation chamber 21a. As illustrated in FIG. 3, the detection mechanism 30 includes a main body portion 31 provided below the accommodation-unit bottom wall 22b, a gas detection sensor 56 (refer to FIG. 5) arranged in the flow path 24a of the bottom extraction port 24, a wiring portion 59 which connects the gas detection sensor 56 and the main body portion 31. The gas detection sensor 56 and a portion of the wiring portion 59 are also a portion of the sensor built-in filter structure 50 described later.

As illustrated in FIG. 3, the main body portion 31 of the detection mechanism 30 is arranged between the accommodation-unit bottom wall 22b and the bottom plate 26 in the height direction which is the Z-axis direction. The thickness of the detection mechanism 30 is equal to smaller than a gap formed between the accommodation-unit bottom wall 22b and the bottom plate 26. The FOUP 20 can be miniaturized by arranging the main body portion 31 by using the vertical gap generated to accommodate the positioning pin 48 and the like provided to the mounting table 46.

Figure 6:
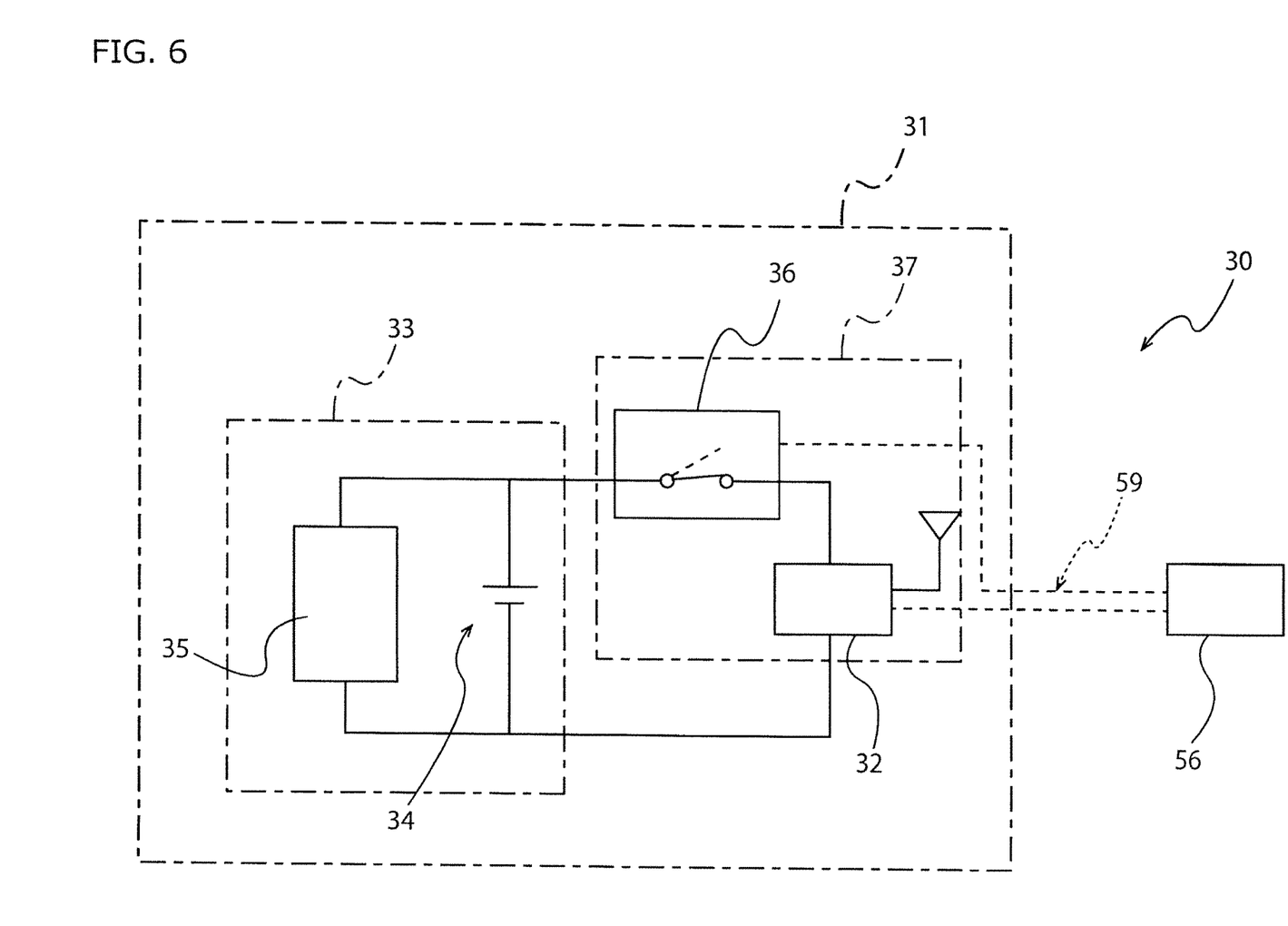
FIG. 6 is a conceptual diagram illustrating a schematic circuit configuration of the detection mechanism illustrated in FIGS. 3 and 4.

FIG. 6 is a conceptual diagram illustrating a schematic circuit configuration of the detection mechanism 30. As illustrated in FIG. 6, the detection mechanism 30 includes a gas detection sensor 56 for detecting a gas contacting the sensor or a gas around the sensor, a data processing unit 37 to which a signal from the gas detection sensor 56 is input, and a power supply unit 33 which supplies power to the gas detection sensor 56 and the data processing unit 37. The data processing unit 37 and the power supply unit 33 are built in the main body portion 31 illustrated in FIG. 2.

Figure 4:
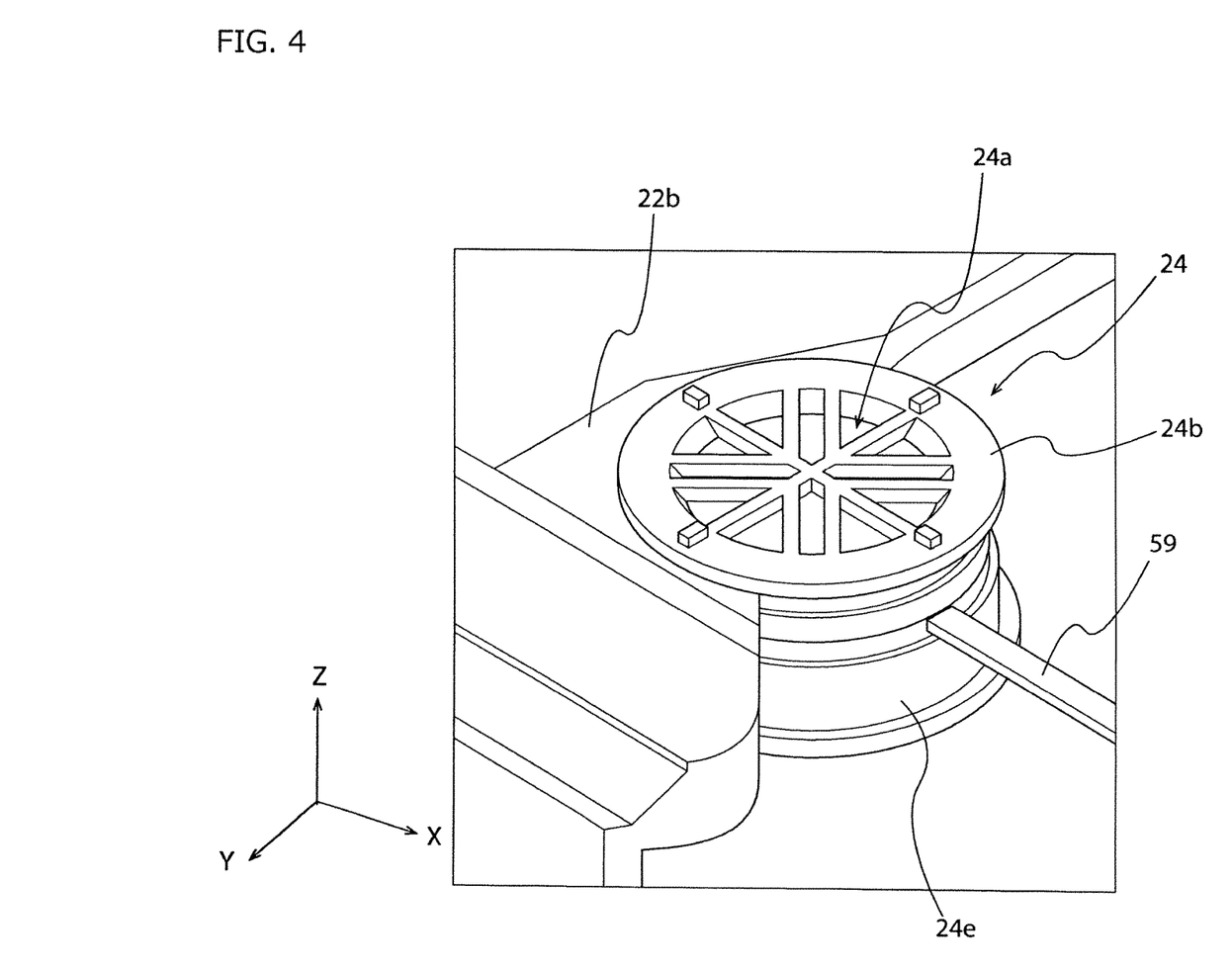
FIG. 4 is a partially enlarged view of a purge port included in the wafer accommodation container illustrated in FIG. 1.
Figure 5:
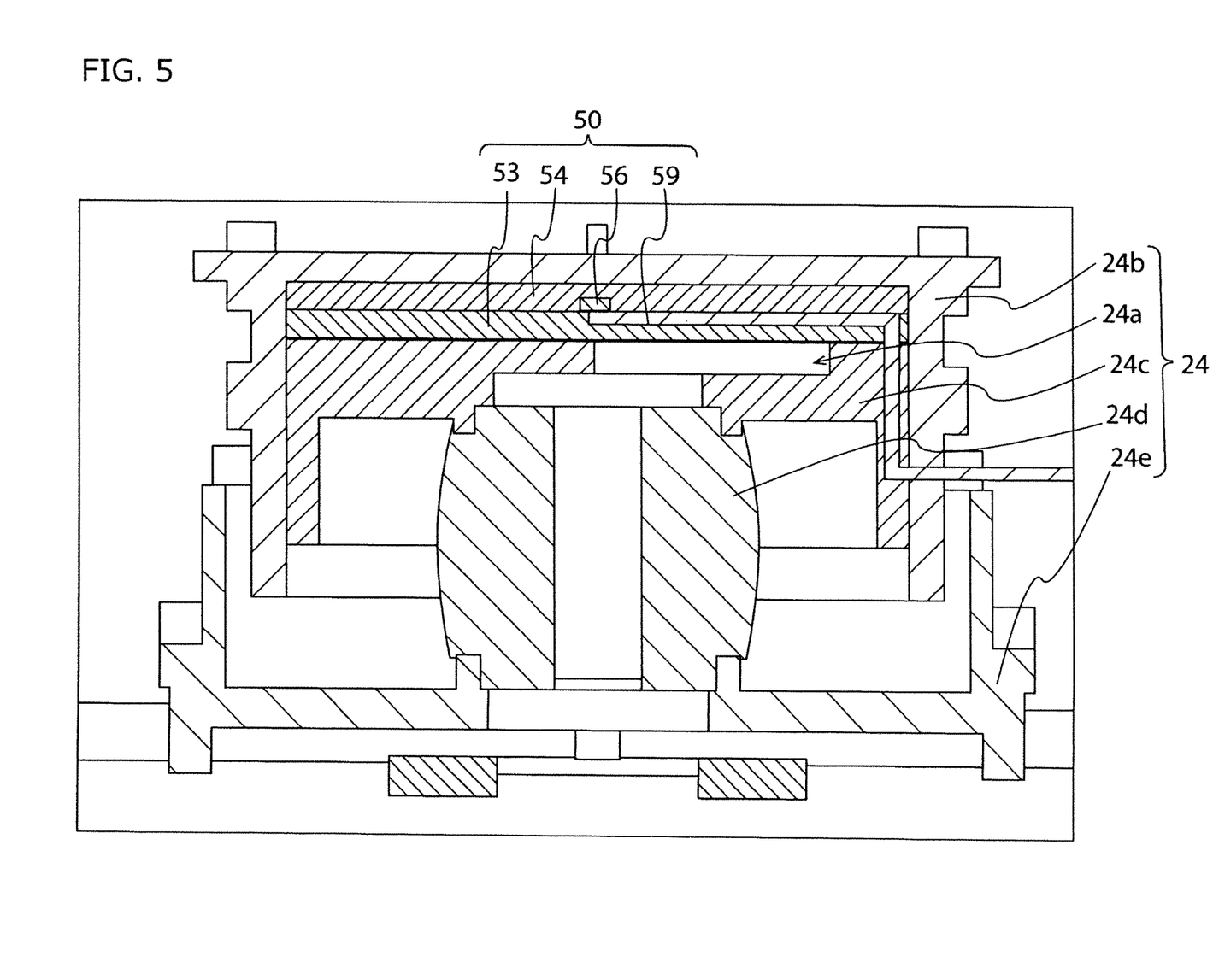
FIG. 5 is a cross-sectional view of a purge port illustrated in FIG. 4 and a sensor built-in filter structure arranged inside the purge port.

FIG. 4 is a partial enlarged view around the bottom extraction port 24 illustrated in FIG. 3. The sensor built-in filter structure 50 including the gas detection sensor 56 which is a portion of the detection mechanism 30 is arranged in the flow path 24a formed inside the bottom extraction port 24. As illustrated in FIG. 4 and FIG. 5 which is a cross-sectional view of the bottom extraction port 24, the bottom extraction port 24 includes an upper body 24b and a lower body 24e in which the flow path 24a is formed, a filter presser 24c, and a check valve 24d.

As illustrated in FIG. 4, the upper body 24b of the bottom extraction port 24 constitutes the upper half of the outer frame of the bottom extraction port 24 and is buried in the through hole formed in the accommodation-unit bottom wall 22b. The upper body 24b has a cylindrical shape, and a plurality of holes or slits are formed in the upper bottom of the upper body 24b so that the gas can move between the wafer accommodation chamber 21a and the flow path 24a of the bottom extraction port 24.

As illustrated in FIG. 4, the lower body 24e of the bottom extraction port 24 constitutes the lower half of the outer frame of the bottom extraction port 24, and the through holes formed in the bottom plate 26 (refer to FIG. 3) are arranged in a portion of the lower body 24e. The lower body 24e has a cylindrical shape which is symmetrical to the upper body 24b, and the through holes are formed in the lower bottom of the lower body 24e so that the gas in the wafer accommodation chamber 21a is discharged through the flow path 24a of the bottom extraction port 24 (refer to FIG. 5).

As illustrated in FIG. 5 which is a cross-sectional view, the filter presser 24c and the check valve 24d are arranged in the space formed by the upper body 24b and the lower body 24e. The check valve 24d is arranged immediately above the through hole of the lower body 24e to prevent an external gas from flowing back to the flow path 24a and the wafer accommodation chamber 21a. The filter presser 24c is arranged immediately above the check valve 24d, and the check valve 24d is vertically interposed between the filter presser 24c and the lower body 24c. Similarly to the upper body 24b illustrated in FIG. 4, through holes or slits are formed in the filter presser 24c, and thus, the gas can pass through the filter presser 24c to flow along the flow path 24a.

As illustrated in FIG. 5, the sensor built-in filter structure 50 is arranged in the flow path 24a connected from the outside to the wafer accommodation chamber 21a. The filter structure 50 includes a first filter 53 which removes dust contained in the gas, a second filter 54 which is arranged closer to the wafer accommodation chamber 21a than to the first filter 53, and a gas detection sensor 56 arranged between the first filter 53 and the second filter 54.

It is preferable that the first filter 53 has a particle collection rate (particle diameter of 0.3 μm) (JIS B 9908: 2011 Type 1) higher than that of the second filter 54. The particle collection rate (particle diameter of 0.3 μm) of the first filter 53 may be, for example, 99.95 to 99.999%. The first filter 53 is not particularly limited as long as the first filter 53 allows the gas to pass and blocks the passage of dust suspended in the semiconductor factory. For example, a quasi HEPA filter, a HEPA filter, a ULPA filter, and other air filters may be employed. It is preferable to employ a HEPA filter.

Similarly to the first filter 53, the second filter 54 allows the gas to pass and blocks the passage of water which is a liquid. It is preferable that the second filter 54 has a water resistance (JIS L 1092: 2009) higher than that of the first filter 53. The water resistance of the second filter 54 may be, for example, 1 to 1000 kpa. In addition, it is preferable that the second filter 54 has pressure loss smaller than that of the first filter 53 from the viewpoint of preventing an air flow resistance from being excessively heightened at the time of the gas passing through the flow path 24a. As the second filter 54, for example, a hydrophobic filter using PTFE, PFA, ETFE, or other fluorine-based resins may be employed.

The gas detection sensor 56 detects at least one of temperature, humidity, pressure, and components of the contacting gas and dust in the gas. As the gas detection sensor 56, a thermometer, an oximeter, a water (water vapor) densitometer, a nitrogen densitometer, a differential pressure gauge, a particle counter, and the like may be exemplified.

Figure 7A:
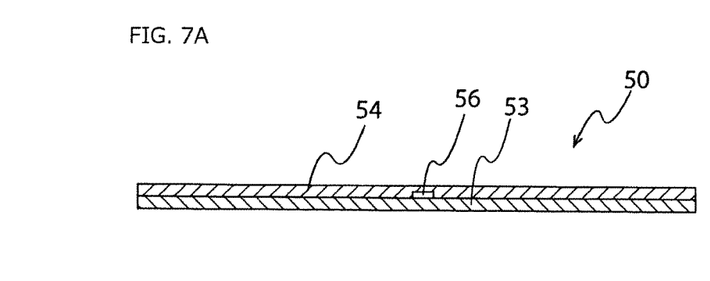
FIGS. 7A to 7D are schematic cross-sectional views illustrating sensor built-in filter structures according to an embodiment and Modified Example.

As illustrated in FIGS. 7A and 5 schematically illustrating the structures of the first and second filters 53 and 54 and the gas detection sensor 56 in the filter structure 50, the first filter 53 and the second filter 54 are overlapped in the filter structure 50 in the vertical direction which is the passing direction of the gas with the gas detection sensor 56 interposed between the first filter 53 and the second filter 54. In addition, as illustrated in FIG. 5, the filter structure 50 is fixed in the flow path 24a by being interposed between the upper bottom of the upper body 24b and the filter presser 24c in the vertical direction. With such a structure, the upper body 24b and the filter presser 24c can collectively support the entire filter structure 50, and the support structure of the filter structure 50 can be configured as a simple structure.

The filter structure 50 includes a portion of the wiring portion 59 which is connected to the gas detection sensor 56 and transmits a detection signal of the gas detection sensor 56 to the main body portion 31 (refer to FIG. 3). One end of the wiring portion 59 is connected to the surface of the gas detection sensor 56 on the side closer to the first filter 53. The wiring portion 59 passes between the first filter 53 and the second filter 54 to be drawn out to the outside of the flow path 24a and to be further drawn out to the outside of the bottom extraction port 24 as illustrated in FIG. 4. Furthermore, the other end portion of the wiring portion 59 is connected to the main body portion 31 as illustrated in FIG. 3.

In addition, as illustrated in FIG. 6, the main body portion 31 can supply power of the power supply unit 33 to the gas detection sensor 56 through the wiring portion 59. Although the wiring portion 59 can be configured with FPC or other printed circuit board or a cable and the like, the wiring portion 59 is not particularly limited.

As illustrated in FIG. 6, the data processing unit 37 includes a transmission unit 32 and a communication control unit 36. The detection result of the gas detection sensor 56 is input to the transmission unit 32 of the data processing unit 37 as an output signal from the gas detection sensor 56. The transmission unit 32 wirelessly transmits the detection result of the gas detection sensor 56 to the reception unit 44 (refer to FIG. 1) of the load port device 40.

The transmission unit 32 illustrated in FIG. 6 may wirelessly transmit the information or the like indicating that the voltage of a power storage unit 34 in the detection mechanism 30 is equal to or higher than a predetermined value besides the detection result of the gas detection sensor 56 to the reception unit 44 (refer to FIG. 1) of the load port device 40. In addition, the transmission unit 32 may also receive a control signal related to the detection mechanism 30 from the reception unit 44 of the load port device 40. Although the transmission unit 32 is configured with a modem, an antenna, and the like, the specific configuration of the transmission unit 32 is not particularly limited.

As illustrated in FIG. 6, the power supply unit 33 has the power storage unit 34 which can perform charging and discharging and a power reception unit 35 which receives energy supplied from the outside to charges the power storage unit 34. For example, as the power storage unit 34, an all-solid battery, an electric double layer capacitor (EDLC), a lithium ion secondary battery, and the like may be exemplified. But, the power storage unit 34 is not particularly limited. The all-solid battery using a solid ceramic material as an electrolyte is preferable from the viewpoint of preventing the contamination of the space and improving the stability. As the power reception unit 35, a power generation element that generates energy by converting energy other than electromagnetic energy into electric energy and a power reception element that receives electromagnetic energy from the outside may be exemplified. As the power generation element, a solar cell, a vibration power generation element, and the like may be exemplified, and as the power reception element, a power reception coil for non-contact charging and the like may be exemplified. The power reception unit 35 according to the embodiment has a power reception coil for non-contact charging corresponding to a power feeding coil included in the power feeding unit 45 illustrated in FIG. 1. The power reception unit 35 illustrated in FIG. 6 can receive supply of power by electromagnetic induction from the power feeding unit 45 provided on the surface of the mounting table 46 in the load port device 40 illustrated in FIG. 1.

The communication control unit 36 in the data processing unit 37 illustrated in FIG. 6 controls the supply of power from the power supply unit 33 to the transmission unit 32 and the gas detection sensor 56. For example, the communication control unit 36 can cut off the supply of power from the power supply unit 33 to the transmission unit 32 during a non-communication period in which the transmission unit 32 does not perform communication. Accordingly, it is possible to reduce the power consumed to maintain the transmission unit 32 in the standby state (sleep state), and thus, it is possible to effectively use the power of the power supply unit 33.

In addition, when the voltage of the power storage unit 34 becomes equal to or higher than a predetermined value, the communication control unit 36 can control the transmission unit 32 so as to wirelessly transmit the information to the reception unit 44 of the load port device 40. With such a configuration, even if the voltage of the power storage unit 34 in the detection mechanism 30 becomes lower than a predetermined value during the transportation together with the FOUP 20, charging is performed through the power feeding unit 45 of the load port device 40, so that in a case where the voltage of the power storage unit 34 is recovered to a predetermined value or more, the operation of the detection mechanism 30 becomes possible.

The communication control unit 36 of the data processing unit 37 controls not only supply of power from the power supply unit 33 to the transmission unit 32 but also supply of power from the power supply unit 33 to the gas detection sensor 56 or operations of the transmission unit 32 and the gas detection sensor 56. The communication control unit 36 is configured with, for example, a microprocessor, but the specific configuration of the communication control unit 36 is not particularly limited.

The reception unit 44 of the load port device 40 illustrated in FIG. 1 and the transmission unit 32 (refer to FIG. 6) provided in the detection mechanism 30 wirelessly communicate the detection result of the gas detection sensor 56 and other control information. The radio frequency used for communication between the reception unit 44 and the transmission unit 32 is not particularly limited. However, the radio frequency may be 2.4 GHz band such as WiFi and Bluetooth (registered trademark) and may be sub-giga Hz (920 MHz band) with a longer communication distance than that of 2.4 GHz band. In addition, with regard to the radio frequency, it is preferable to use infrared communication standardized as an IrDA standard or the like. This is because, although infrared transmission may be inferior in transmission rate to other methods, since the communication range is limited, the infrared transmission is less affected by interference with wireless communication in other frequency bands that can be used in the factory, and the infrared transmission can prevent other radio communication from being affected by interference or the like.

The detection result of the gas detection sensor 56 can be used, for example, to determine whether or not to the cleaning process of the wafer accommodation chamber 21a by the load port device 40 or can be used for controlling the quality of the wafer 10. However, the method using the detection result is not particularly limited.

As described above, in the sensor built-in filter structure 50 (refer to FIG. 5 and the like) arranged in the flow path 24a of the bottom extraction port 24, the gas detection sensor 56 is arranged between the two filters of the second filter 54 which is a waterproof ventilation filter and the first filter 53 which is a dustproof filter. Accordingly, the filter structure 50 can bring the gas in the wafer accommodation chamber 21a into contact with the gas detection sensor 56 to detect the gas in the wafer accommodation chamber 21a and, at the same time, to allow the second filter 54 to prevent the entry of water from the chamber, so that it is possible to prevent the gas detection sensor 56 from being wet with a liquid such as water even at the time of rinsing the wafer accommodation chamber 21a by using the liquid such as water.

In addition, since the main body portion 31 of the detection mechanism 30 is arranged outside the flow path 24a of the bottom extraction port 24 through the wiring portion 59, in the FOUP 20, the main body portion 31 is prevented from being wet by water at the time of rinsing the wafer accommodation chamber 21a. Therefore, in the FOUP 20, there is no need to remove the sensor built-in filter structure 50 and the detection mechanism 30 at the time of rinsing the wafer accommodation chamber 21a, and thus, the sensor built-in filter structure 50 can maintain good maintenance performance of the FOUP 20.

In addition, since the sensor built-in filter structure 50 includes the first filter 53, it is possible to prevent the problem in that the dust in the wafer accommodation chamber 21a flows out to the outside, and it is possible to prevent the problem the dust from the outside flows into the wafer accommodation chamber through the flow path 24a. In addition, since the flow path 24a in which the filter structure 50 is provided is a portion of the bottom extraction port 24 for discharging the gas from the wafer accommodation chamber 21a, any flow path for detecting the gas need not be separately provided to the FOUP 20, which is advantageous from the viewpoint of miniaturization, and the gas in the wafer accommodation chamber 21a can be suitably detected even during purge for cleaning the wafer accommodation chamber 21a.

In addition, the filter structure 50 may be arranged in the flow path of the bottom introduction port 25 for introducing the cleaning gas into the wafer accommodation chamber 21a. Even with such a structure, the gas in the wafer accommodation chamber 21a can be suitably detected except for the time of introducing the cleaning gas from the bottom introduction port 25 into the wafer accommodation chamber 21a.

Heretofore, although the invention has been described with reference to the embodiments, the invention is not limited to only these embodiments, and there are many other embodiments and Modified Examples. For example, the wafer accommodation container which transports the wafer 10 is not limited to the FOUP 20, and the filter structure 50 may be provided to different containers such as a FOSB for transporting the wafer 10. In addition, the wafers stored in wafer accommodation container include not only the silicon wafers used for so-called semiconductor manufacturing but also other semiconductor substrates and thin plate materials such as glass substrates used for manufacturing liquid crystal panels other than semiconductor substrates.

Figure 7B:
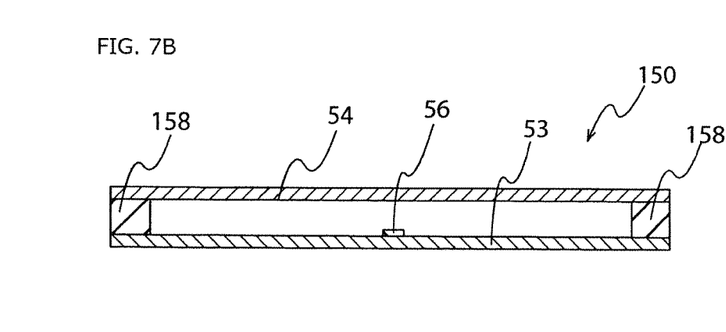

FIG. 7B is a schematic cross-sectional view illustrating a sensor built-in filter structure 150 according to Modified Example 1 of the invention. Instead of the filter structure 50 illustrated in FIG. 7A, a filter structure 150 illustrated in FIG. 7B may be arranged in the flow path 24a of the FOUP 20 illustrated in FIG. 1. Similarly to the filter structure 50, the filter structure 150 includes a first filter 53, a second filter 54 arranged closer to a wafer accommodation chamber 21a than to the first filter 53, and a gas detection sensor 56.

However, in the filter structure 150, the first filter 53 and the second filter 54 are arranged with a predetermined interval with the spacer 158 interposed between the first filter 53 and the second filter 54, and the gas detection sensor 56 is provided on the surface of the first filter 53 on the side closer to the wafer accommodation chamber 21a. In comparison to the filter structure 50 illustrated in FIG. 7A, in the filter structure 150, since the first filter 53 and the second filter 54 are arranged with a predetermined interval, the first filter 53 is hard to be wet by water from the wafer accommodation chamber 21a side.

In addition, since water from the wafer accommodation chamber 21a side is hard to enter the filter structure 150 illustrated in FIG. 7B, the second filter 54 is configured to be thinner, so that it is possible to reduce pressure loss in the entire filter structure 150. In addition, the gas detection sensor 56 also has a structure in which the gas detection sensor 56 is spaced apart from the second filter 54, so that the gas detection sensor 56 is hard to be wet with water from the wafer accommodation chamber 21a. Besides, the sensor built-in filter structure 150 has effects similar to those of the filter structure 50 illustrated in FIG. 7A.

Figure 7C:
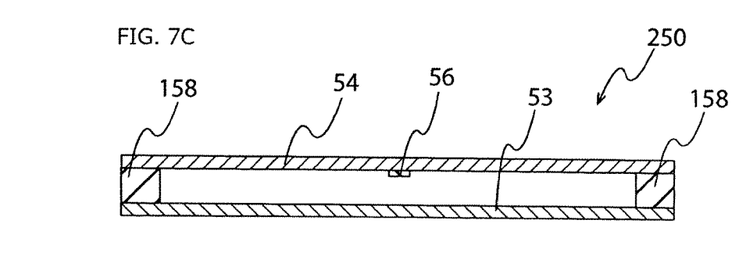

FIG. 7C is a schematic cross-sectional view illustrating a sensor built-in filter structure 250 according to Modified Example 2 of the invention. The filter structure 250 is the same as the filter structure 150 according to Modified Example 1 except that the gas detection sensor 56 is provided on the surface of the second filter 54 on the side opposite to the wafer accommodation chamber 21a. In the filter structure 250, the gas detection sensor 56 can be arranged closer to the wafer accommodation chamber 21a than the filter structure 150 illustrated in FIG. 7B. Besides, the filter structure 250 has effects similar to those of the filter structures 50 and 150.

Figure 7D:
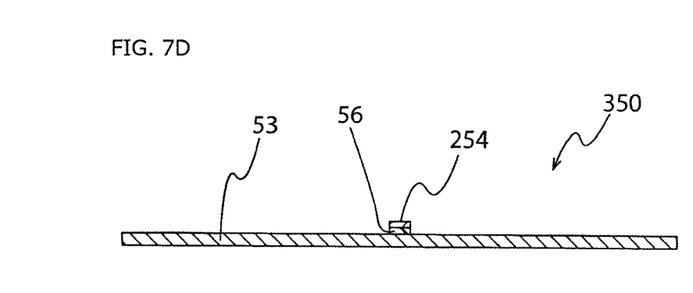

FIG. 7D is a schematic cross-sectional view illustrating a sensor built-in filter structure 350 according to Modified Example 3 of the invention. The filter structure 350 is the same as the filter structure 50 according to the embodiment except that the second filter 354 has a smaller area than the first filter 53 and is provided on the surface of the gas detection sensor 56 on the side closer to the wafer accommodation chamber 21a. In the filter structure 350, since the area of the second filter 54 can be configured to be smaller than that of the filter structure 50 illustrated in FIG. 7A, the pressure loss in the entire filter structure 350 can be reduced. In addition, the filter structure 350 has effects similar to those of as the filter structure 50.

DESCRIPTION OF THE REFERENCE NUMERALS

10 . . . wafer
20 . . . FOUP
21 . . . wafer accommodation unit
22 . . . housing unit
22a . . . main opening
22b . . . accommodation-unit bottom wall
23 . . . lid
24 . . . bottom extraction port
24a . . . flow path
24b . . . upper body
24c . . . filter presser
24d . . . check valve
24e . . . lower body
25 . . . bottom introduction port
26 . . . bottom plate
30 . . . detection mechanism
31 . . . main body portion
32 . . . transmission unit
33 . . . power supply unit
34 . . . power storage unit
35 . . . power reception unit
36 . . . control unit
37 . . . data processing unit
50 . . . sensor built-in filter structure
53 . . . first filter
54, 354 . . . second filter
56 . . . gas detection sensor
59 . . . wiring portion
40 . . . load port device
41 . . . front purge nozzle
42 . . . bottom purge nozzle
43 . . . control unit
44 . . . reception unit
45 . . . power feeding unit
46 . . . mounting table
47 . . . door
48 . . . positioning pin
60 . . . EFEM
62 . . . transfer robot
64 . . . wall portion
66 . . . wafer transfer chamber

What is claimed is:

1. A sensor built-in filter structure arranged in a wafer accommodation container, comprising:
   a first filter;
   a second filter arranged closer to a wafer accommodation chamber of the wafer accommodation container than to the first filter; and
   a gas detection sensor arranged between the first filter and the second filter to detect a state of a gas,
   wherein the first filter and the second filter are overlapped with the gas detection sensor interposed between the first filter and the second filter.

2. The sensor built-in filter structure according to claim 1, wherein the first filter removes dust contained in the gas.

3. The sensor built-in filter structure according to claim 1, wherein the first filter has a particle collection rate higher than that of the second filter.

4. The sensor built-in filter structure according to claim 1, wherein the second filter blocks passage of water as a liquid and allows the gas to pass.

5. The sensor built-in filter structure according to claim 1, wherein the second filter has a water resistance higher than that of the first filter.

6. The sensor built-in filter structure according to claim 1, wherein the state detected by the gas detection sensor is at least one of temperature, humidity, pressure and component of the gas or the dust in the gas.

7. The sensor built-in filter structure according to claim 1, wherein the second filter has a smaller area than the first filter and is provided on a surface of the gas detection sensor on a side closer to the wafer accommodation chamber.

8. A wafer accommodation container comprising:
the sensor built-in filter structure according to claim 1;
the wafer accommodation chamber; and
a purge port having the flow path for introducing a cleaning gas into the wafer accommodation chamber or for discharging the gas from the wafer accommodation chamber.

9. The wafer accommodation container according to claim 8, wherein the flow path provided with the sensor built-in filter structure is a portion of the purge port for discharging the gas from the wafer accommodation chamber.

10. A sensor built-in filter structure arranged in a wafer accommodation container, comprising:
a first filter;
a second filter arranged closer to a wafer accommodation chamber of the wafer accommodation container than to the first filter; and
a gas detection sensor arranged between the first filter and the second filter to detect a state of a gas, wherein
the sensor built-in filter structure is in a flow path connected from an outside to the wafer accommodation chamber,
the first filter and the second filter are arranged with a predetermined interval, and
the gas detection sensor is provided on a surface of the first filter on a side closer to the wafer accommodation chamber.

11. A wafer accommodation container comprising:
the sensor built-in filter structure according to claim 10;
the wafer accommodation chamber; and
a purge port having the flow path for introducing a cleaning gas into the wafer accommodation chamber or for discharging the gas from the wafer accommodation chamber.

12. The wafer accommodation container according to claim 11, wherein the flow path provided with the sensor built-in filter structure is a portion of the purge port for discharging the gas from the wafer accommodation chamber.

13. A sensor built-in filter structure arranged in a wafer accommodation container, comprising:
a first filter;
a second filter arranged closer to a wafer accommodation chamber of the wafer accommodation container than to the first filter; and
a gas detection sensor arranged between the first filter and the second filter to detect a state of a gas, wherein
the sensor built-in filter structure is in a flow path connected from an outside to the wafer accommodation chamber,
the first filter and the second filter are arranged with a predetermined interval, and
the gas detection sensor is provided on a surface of the second filter on a side opposite to the wafer accommodation chamber.

14. A wafer accommodation container comprising:
the sensor built-in filter structure according to claim 13;
the wafer accommodation chamber; and
a purge port having the flow path for introducing a cleaning gas into the wafer accommodation chamber or for discharging the gas from the wafer accommodation chamber.

15. The wafer accommodation container according to claim 14, wherein the flow path provided with the sensor built-in filter structure is a portion of the purge port for discharging the gas from the wafer accommodation chamber.

* * * * *